United States Patent [19]
Vibe-Hansen et al.

[11] Patent Number: 6,120,514
[45] Date of Patent: *Sep. 19, 2000

[54] METHOD AND KIT FOR AUTOLOGOUS TRANSPLANTATION

[75] Inventors: Henrik Vibe-Hansen, Lyngby; Charlotte Lundsgaard, Klampenborg, both of Denmark; Kurt B. Osther, Scottsdale, Ariz.

[73] Assignee: VTS Holdings, LLC, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/088,142

[22] Filed: Jun. 1, 1998

Related U.S. Application Data

[63] Continuation-in-part of application No. 08/704,891, Aug. 30, 1996, Pat. No. 5,759,190.

[51] Int. Cl.[7] ................................................ A61B 17/08
[52] U.S. Cl. ............................................................ 606/151
[58] Field of Search ................................... 606/151, 214; 623/11, 13, 16, 1

[56] References Cited

U.S. PATENT DOCUMENTS 5,759,190  6/1998  Vibe-Hasen et al. ................. 606/151

*Primary Examiner*—Michael Buiz
*Assistant Examiner*—Vy Q. Bui
*Attorney, Agent, or Firm*—Ratner & Prestia

[57] ABSTRACT

Methods for effective chondrocyte and/or cartilage transplantation to articulating joint surfaces are taught, and a kit providing materials for the practice of the method is described.

9 Claims, 2 Drawing Sheets

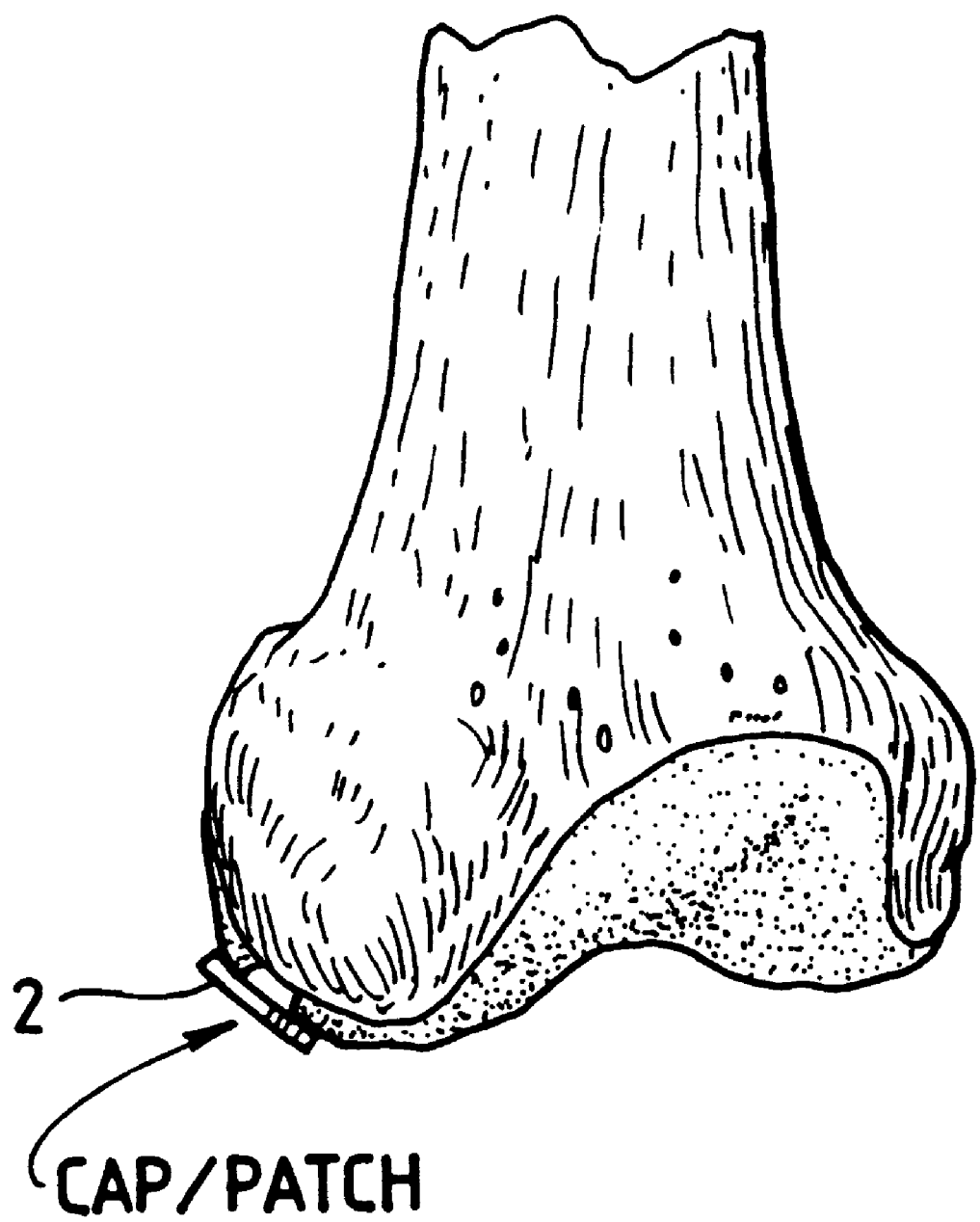

METHOD AND KIT FOR AUTOLOGOUS TRANSPLANTATION

RELATED APPLICATION

This application is a continuation-in-part of U.S. patent application Ser. No. 08/704,891 filed Aug. 30, 1996, now U.S. Pat. No. 5,759,190.

FIELD OF THE INVENTION

The instant invention concerns the field of chondrocyte transplantation, bone and cartilage grafting, healing, joint repair and the prevention of arthritic pathologies.

BACKGROUND OF THE INVENTION

More than 500,000 arthroplastic procedures and total joint replacements are performed each year in the United States. Approximately the same number of similar procedures are performed in Europe. Included in these numbers are about 90,000 total knee replacements and around 50,000 procedures to repair defects in the knee per year (In: Praemer A., Furner S., Rice, D. P., Musculoskeletal conditions in the United States, Park Ridge, Ill.: American Academy of Orthopaedic Surgeons, 1992, 125). A method for regeneration-treatment of cartilage would be most useful, and could be performed at an earlier stage of a joint damage, thus reducing the number of patients needing artificial joint replacement surgery. With such preventative methods of treatment, the number of patients developing osteoarthritis would also decrease.

Techniques used for resurfacing the cartilage structure in joints have mainly attempted to induce the repair of cartilage using subchondral drilling, abrasion and other methods whereby there is excision of diseased cartilage and subchondral bone, leaving vascularized cancellous bone exposed (Insall, J., Clin. Orthop. 1974, 101, 61; Ficat R. P. et al, Clin Orthop. 1979, 144, 74; Johnson L. L., In: (McGinty J. B., Ed.) Operative Arthroscopy, New York: Raven Press, 1991, 341).

Coon and Cahn (1966, Science 153: 1116) described a technique for the cultivation of cartilage synthesizing cells from chick embryo somites. Later Cahn and Lasher (1967, PNAS USA 58: 1131) used the system for analysis of the involvement of DNA synthesis as a prerequisite for cartilage differentiation. Chondrocytes respond to both EGF and FGF by growth (Gospodarowicz and Mescher, 1977, J. Cell Physiology 93: 117), but ultimately lose their differentiated function (Benya et al., 1978, Cell 15: 1313). Methods for growing chondrocytes were described and are principally being used with minor adjustments as described by (Brittberg, M. et al., New Engl. J. Med. 1994, 331, 889). Cells grown using these methods were used as autologous transplants into knee joints in patients. Additionally, Kolettas et al. examined the expression of cartilage-specific molecules such as collagens and proteoglycans under prolonged cell culturing. They found that despite morphological changes during culturing in monolayer cultures (Aulthouse, A. et al., In Vitro Cell Dev. Biol., 1989, 25, 659; Archer, C. et al., J. Cell Sci. 1990, 97, 361; Hänselmann, H. et al., J. Cell Sci. 1994, 107, 17; Bonaventure, J. et al., Exp. Cell Res. 1994, 212, 97) when compared to suspension cultures grown over agarose gels, alginate beads or as spinner cultures (retaining a round cell morphology) the expressed markers such as types II and IX collagens and the large aggregating proteoglycans, aggrecan, versican and link protein did not change.(Kolettas, E. et al., J. Cell Science 1995, 108, 1991).

The articular chondrocytes are specialized mesenchymal derived cells found exclusively in cartilage. Cartilage is an avascular tissue whose physical properties depend on the extracellular matrix produced by the chondrocytes. During endochondral ossification chondrocytes undergo a maturation leading to cellular hypertrophy, characterized by the onset of expression of type X collagen (Upholt, W. B. and Olsen, R. R., In: Cartilage Molecular Aspects (Hall, B & Newman, S, Eds.) CRC Boca Raton 1991, 43; Reichenberger, E. et al., Dev. Biol. 1991, 148, 562; Kirsch, T. et al., Differentiation, 1992, 52, 89; Stephens, M. et al., J. Cell Sci. 1993, 103, 1111).

Despite the advances in cultivating chondrocytes, and manipulating bone and cartilage, there has not been great success with the attempts to transplant cartilage or chondrocytes for the repair of damaged articulating surfaces. The teachings of the insant invention provide for effective, and efficient means of promoting the transplantation of cartilage and/or chondrocytes into a defect in an articulating joint whereby cartilage is regenerated to fix the defect.

BRIEF SUMMARY OF THE INVENTION

The instant invention provides a method for the effective treatment of articulating joint surface cartilage by the transplantation of chondrocytes in a suitable matrix, to a surface to be treated, with a hemostatic barrier and a cell-free covering-patch comprising; first placing a hemostatic barrier proximal to the surface to be treated, placing chondrocytes in a suitable matrix upon the surface to be treated distal to the hemostatic barrier, covering the surface to be treated with a cell-free covering-patch. In particular, a method wherein the hemostatic barrier is a resorbable semi-permeable material which inhibits or prohibits vascular infiltration through the barrier. In another embodiment, the method encompasses where the cell-free covering-patch is a semi-permeable collagen matrix. In another embodiment the invention encompasses a method wherein the hemostatic barrier contains collagen. In one preferred embodiment the invention embodies a method wherein the porous surface of the patch is directed towards the implant.

The instant invention further provides for a kit for cartilage and/or chondrocyte transplantation onto the surface of an articular joint wherein said kit comprises a hemostatic barrier, cell-free semi-permeable covering-patch, and organic glue.

BRIEF DESCRIPTION OF THE DRAWINGS

FIG. 2 is a drawing showing the treated defect (gap in cross hatched area) in the cartilagenous cap (cross hatched) covered by a cell-free semi-permeable material (solid black) which is used to form a cap/patch or bandage over the defect site. This cap is fixed in place, either sutured to the edge of the cavity into healthy cartilage or otherwise attached. This cap is covering the defective area of the joint into which the cultured chondrocytes have been transplanted.

DETAILED DESCRIPTION OF THE INVENTION

Figure 1A:
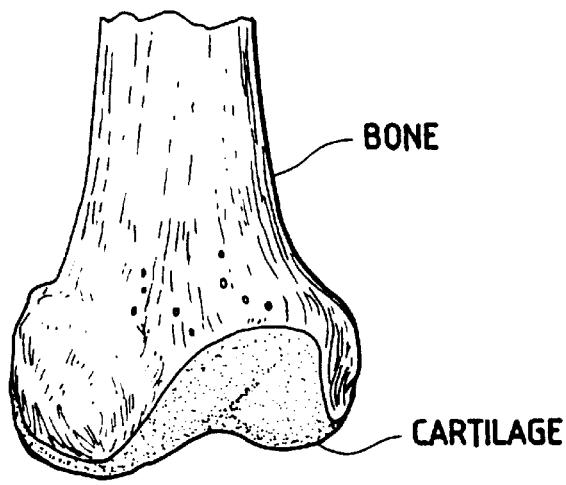
FIG. 1 A is a drawing showing a typical articulating end of a bone. Typically, the bone material is covered on the articulating surface with a cartilagenous cap (shown by cross-hatching). Where a defect or injury to the cartilagenous cap occurs (Gap in cartilage cap of FIG. 1 B), the defective site can be treated directly, or enlarged slightly by surgical procedures. The hemostatic barrier (Solid Black) is placed within the defect in the cartilage cap to inhibit or prevent vascularization into regenerating cartilage from the underlying bone (FIG. 1 C). The chondrocytes to be implanted into the defect cavity are then layered on top of this hemostatic barrier.
Figure 1B:
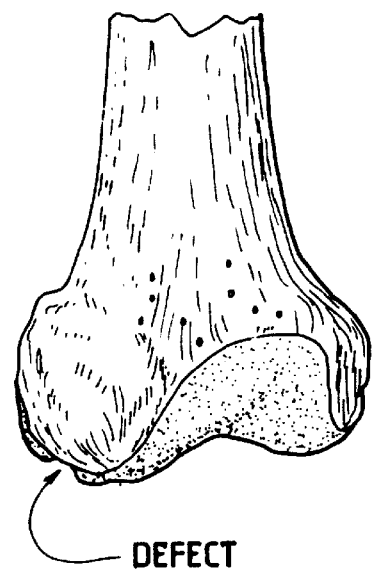
Figure 1C:
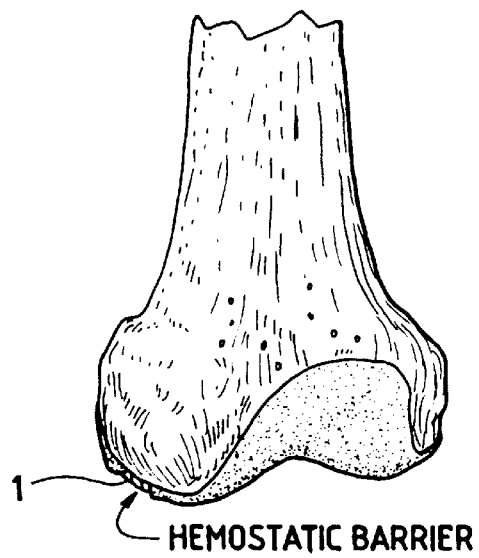

This invention concerns the use of certain products that inhibit the formation of vascular tissue, for instance such as capillary loops projecting into the cartilage being established, during the process of autologous transplantation of chondrocytes into defects in the cartilage. The formation of vascular tissue from the underlying bone will tend to project into the new cartilage to be formed leading to appearance of cells other than the mesenchymal specialized chondrocytes desired.

The contaminating cells introduced by the vascularization may give rise to encroachment and over-growth into the cartilage to be formed by the implanted chondrocytes. One of the types of commercial products which can be used in this invention is Surgicel® (Ethicon Ltd., UK) which is absorbable after a period of 7–14 days. This is contrary to the normal use of a hemostatic device, such as Surgicel, as described in the insert from Ethicon Ltd.

Suprisingly, we have found that in a situation where you wish to inhibit the re-vascularization into cartilage, a hemostatic material will act as a gel like artificial coagulate. If red blood cells should be present within the full-thickness defect of articular cartilage that is capped by such a hemostatic barrier, these blood cells will be chemically changed to hematin and thus not be able to induce vascular growth. Thus, a hemostatic product used as a re-vascularization inhibitory barrier with or without fibrin adhesives, such as for example the Surgicel, is effective for the envisioned method as taught by the instant invention. Another part of this invention is the use of a cell-free component, that is used as a patch covering the defective area of the joint into which the cultured chondrocytes are being transplanted using autologous chondrocytes for the transplantation. The same two parts of the invention may also be utilized if it appears that one could use certain allogeneic chondrocytes or xenogeneic chondrocytes for the repair of a cartilage defect.

Thus the instant invention teaches methods for effective repair or treatment of cartilage defects in articular joint bone surfaces which comprises administering an agent or device to block vascular invasion of the cartilage site to be repaired, and also providing for a cell-free barrier which will isolate the repair site and keep transplanted cells in place. Thus the instant invention also provides for a kit comprising a hemostatic component for insertion into the site to be repaired such that there is an effective inhibition of vascularization into the site to be repaired; and once the chondrocytes to be transplanted are placed into the site to be repaired, a cell-free semi-permeable barrier is capped over the repair site such that the transplanted chondrocytes are held in place, but are still able to gain access to nutrients.

Certain aspects of the invention has been exemplified using an in vitro system to study the behavior of the chondrocytes when in contact with a certain product or a combination of certain products that will inhibit the formation of vascular tissue. This in vitro testing predicts the ability of certain tested materials to inhibit vascularization, as will occur in vivo where capillary loops project into the cartilage being established during the process of autologous transplantation of chondrocytes into defects in the cartilage.

Suitable hemostatic products will be characterized by having the ability to inhibit the growth, or invasion of vascular tissue, osteocytes, fibroblasts, etc. into the developing cartilage. A suitable hemostatic material will achieve the goal of the methods of the instant invention in that vascular and cellular invasion into developing cartilage should be prevented in order to optimize the formation of cartilage and achieve repair of the full-thickness of any defects in the articular cartilage. Ideally, the hemostatic barrier will be stable for an extended period of time sufficient to allow for full cartilage repair, and then be able to be absorbed or otherwise broken down over time. One material identified as suitable is called Surgicel® W1912 (Lot GG3DH, Ethicon Ltd. UK), and is an absorbable hemostat such as oxidized regenerated sterile cellulose.

Certain aspects of the instant invention may be better understood as illustrated by the following examples.

EXAMPLE 1

In order for the Surgicel® to be used according to our invention in preventing development of blood vessels into autologous implanted cartilage or chondrocytes, we treated the Surgicel® with a fixative, such as glutaric aldehyde; we have chosen 0.6% glutaric aldehyde treatment of the Surgicel® for 1 minute, followed by washings to eliminate glutaric aldehyde residues that may otherwise be toxic to tissue. Alternatively, the Surgicel® was treated with the fibrin adhesive called Tisseel® (Immuno AG, Vienna, Austria)), prior to treatment with glutaric aldehyde as described in example 2. We found that the Surgicel® fixated for instance with a fixative such as glutaric aldehyde, washed with sterile physiological saline (0.9%) and stored in refrigerator, does not dissolve for 1 to 2 months. Generally, Surgical is resorbed in a period between 7 and 14 days. This time would be too short, because a longer time is needed in preventing the development of blood vessels or vascularization as such from the bone structure into the implanted cartilage before the implanted chondrocytes have grown into a solid cartilage layer getting its nutrition requirements from the neighboring cartilage. In other words sufficient inhibition of the vascularization is needed for a longer time such as for instance one month. Therefore, the product should not be absorbed significantly prior to that time. On the other hand resorption is needed eventually. Hence, the organic material used as an inhibiting barrier shall have these capabilities, and we have found that the Surgicel® treated in this manner provides that function.

EXAMPLE 2

The Surgicel® was also coated with an organic glue, in this case we have used Tisseel® as a glue. This product, together with the Surgicel® produces a useable barrier for our particular purpose. Any other hemostatic or vascular inhibiting barrier could be used. The Tisseel® was mixed as described below. The Surgicel® was then coated with Tisseel® by spraying Surgicel® on both sides until soaked. The Tisseel® (fibrin glue) was then allowed to solidify in room temperature. Immediately prior to completed solidification, the Surgicel® was then placed in 0.6% glutaric aldehyde for 1 minute and then washed with sterile physiological (0.9%) saline. The pH was then adjusted by PBS and/or with NaOH until pH was stable at 7.2 to 7.4. Afterwards the thus treated Surgicel® was then washed in tissue culture medium such as minimum essential medium/F12 with 15 mM Hepes buffer.

As mentioned in this example we have used Tisseel® as the fibrin adhesive to coat the Surgicel®. Furthermore the fibrin adhesive or glue may also be applied directly on the bottom of the lesion towards the bone, on which the Surgicel® is glued. The in vitro system used, in lieu of in vivo testing, consisted of a NUNCLON™ Delta 6-well sterile disposable plate for cell research work (NUNC (InterMed) Roskilde, Denmark). Each well measures approximately 4 cm in diameter.

In the invention the fibrin adhesive can be any adhesive which together with the fibrin component will produce a glue that can be tolerated in humans (Ihara, N, et al., Burns Incl. Therm. Inj., 1984 10,396). The invention also anticipates any other glue component that can be used in lieu of the fibrin adhesive. In this example we used Tisseel® or Tissucol® (Immuno AG, Vienna, Austria). The Tisseel® kit consists of the following components:

Tisseel®, a lyophilized, virus-inactivated Sealer, containing clottable protein, thereof: fibrinogen, Plamafibronectin (CIG) and Factor XIII, and Plasminogen.

Aprotinin Solution (bovine)

Thrombin 4 (bovine)

Thrombin 500 (bovine)

Calcium Chloride solution

The Tisseel® kit contains a DUPLOJECT® Application System. The fibrin adhesive or the two-component sealant using Tisseel® Kit is combined in the manner according to Immuno AG product insert sheet.

EXAMPLE 3

Chondrocytes were grown in minimal essential culture medium containing HAM F12 and 15 mM Hepes buffer and 5 to 7.5% autologous serum in a $CO_2$ incubator at 37° C. and handled in a Class 100 laboratory at Verigen Europe A/S, Symbion Science Park, Copenhagen, Denmark. Other compositions of culture medium may be used for culturing the chondrocytes. The cells were trypsinized using trypsin EDTA for 5 to 10 minutes and counted using Trypan Blue viability staining in a Bürker-Türk chamber. The cell count was adjusted to $7.5 \times 10^5$ cells per ml. One NUNCLON plate was uncovered in the Class 100 laboratory.

The Surgicel® hemostatic barrier was cut to a suitable size fitting into the bottom of the well in the NUNCLON tissue culture tray. In this case a circle, of a size of approximately 4 cm (but could be of any possible size) and placed under aseptic conditions on the bottom in well in a NUNCLON™ Delta 6 well sterile disposable plate for cell research work (NUNC (InterMed) Roskilde, Denmark). The hemostatic barrier to be placed on the bottom of the well was pre-treated as described in Example 1. This treatment delays the absorption of the Surgicel® significantly. This hemostatic barrier was then washed several times in distilled water and subsequently several times until non-reacted glutaraldehyde was washed out. A small amount of the cell culture medium containing serum was applied to be absorbed into the hemostatic barrier and at the same time keeping the hemostatic barrier wet at the bottom of the well.

A number of approximately $10^6$ cells in 1 ml culture medium were placed directly on top of the hemostatic barrier, dispersed over the surface of the hemostatic barrier, pre-treated with 0.4% glutaraldehyde as described above. The plate was then incubated in a $CO_2$ incubator at 37° C. for 60 minutes. An amount of 2 to 5 ml of tissue culture medium containing 5 to 7.5% serum was carefully added to the well containing the cells avoiding splashing the cells by holding the pipette tip tangential to the side of the well when expelling the medium. It appeared that the pH of the medium was too low (pH ~6.8). The pH was then adjusted to 7.4 to 7.5. The next day some chondrocytes had started to grow on the hemostatic barrier, arranged in clusters. Some of the cells had died due to the low pH exposure prior to the adjustment of the pH. The plate was incubated for 3 to 7 days with medium change at day 3.

At the end of the incubation period the medium was decanted and cold refrigerated 2.5% glutaraldehyde containing 0.1M sodium salt of dimethylarsinic acid, also called sodium cacodylate, pH is adjusted with HCl to 7.4, was added as fixative for preparation of the cell and supporter (hemostatic barriert) for later preparation for electron microscopy.

EXAMPLE 4

Chondrocytes were grown in minimal essential culture medium containing HAM F12 and 15 mM Hepes buffer and 5 to 7.5% autologous serum in a $CO_2$ incubator at 37° C. and handled in a Class 100 laboratory at Verigen Europe A/S, Symbion Science Park, Copenhagen, Denmark. Other compositions of culture medium may be used for culturing the chondrocytes. The cells were trypsinized using trypsin EDTA for 5 to 10 minutes and counted using Trypan Blue viability staining in a Bürker-Türk chamber. The cell count was adjusted to $7.5 \times 10^5$ cells per ml. One NUNCLON plate was uncovered in the Class 100 laboratory.

The Surgicel® (for use as a hemostatic barrier) was treated with 0.6% glutaric aldehyde for one minute as described in Example 1, and washed with 0.9% sterile sodium chloride solution or, preferably, with a buffer such as a PBS buffer or the culture medium such as MEM/F12, because pH after the glutaric aldehyde treatment is 6.8 and should preferably be 7.0 to 7.5. The Tisseel® was applied on both side of the Surgicel® using the DUPLOJECT® system, thus coating both sides of the Surgicel®, the patch intended to be used, with fibrin adhesive. The glue is left to dry under aseptic condition for at least 3 to 5 minutes. The "coated" hemostatic barrier was placed on the bottom of the well in a NUNCLON™ Delta 6-well sterile disposable plate for cell research work (NUNC (InterMed) Roskilde, Denmark). A small amount of tissue culture medium containing serum was applied to be absorbed into the hemostatic barrier. A number of approximately $10^6$ cells in 1 ml tissue culture medium containing serum was placed directly on top of the hemostatic barrier, dispersed over the surface of the hemostatic barrier. The plate was then incubated in a $CO_2$ incubator at 37° C. for 60 minutes. An amount of 2 to 5 ml of tissue culture medium containing 5 to 7.5% serum was carefully added to the well containing the cells avoiding splashing the cells by holding the pipette tip tangential to the side of the well when expelling the medium. After 3 to 6 days microscopic examination showed that the cells were adhering to and growing into the Surgicel® in a satisfactory way suggesting that Surgicel® did not show toxicity to the chondrocytes and that the chondrocytes grew in a satisfactory manner into the Surgicel®.

The plate was incubated for 3 to 7 days with medium change at day 3. At the end of the incubation period the medium was decanted and cold refrigerated 2.5% glutaraldehyde containing 0.1M sodium salt of dimethylarsinic acid, also called sodium cacodylate, pH is adjusted with HCl to 7.4, was added as fixative for preparation of the cell and supporter (hemostatic barrier) for later preparation for electron microscopy.

EXAMPLE 5

Chondrocytes were grown in minimal essential culture medium containing HAM F12 and 15 mM Hepes buffer and 5 to 7.5% autologous serum in a $CO_2$ incubator at 37° C. and handled in a Class 100 laboratory at Verigen Europe A/S, Symbion Science Park, Copenhagen, Denmark. The cells were trypsinized using trypsin EDTA for 5 to 10 minutes and counted using Trypan Blue viability staining in a Bürker-Türk chamber. The cell count was adjusted to $7.5 \times 10^5$ to $2 \times 10^6$ cells per ml. One NUNCLON plate was uncovered in the Class 100 laboratory.

The Bio-Gide® is a resorbable bilayer membrane which will be used as the patch or bandage covering the defective area of the joint into which the cultured chondrocytes are being transplanted by autologous transplantation. The Bio-Gide® is a pure collagen membrane obtained by standardized, controlled manufacturing processes by E. D. Geistlich Söhne AG, CH-6110 Wolhusen. The collagen is extracted from veterinary certified pigs and is carefully purified to avoid antigenic reactions, and sterilized in double blisters by γ-irradiation. The bilayer membrane has a porous surface and a dense surface. The membrane is made of collagen type I and type III without further cross-linking or chemical treatment. The collagen is resorbed within 24 weeks. The membrane retains its structural integrity even when wet and it can be fixed by sutures or nails. The membrane may also be "glued" using fibrin adhesive such as Tisseel® to the neighbouring cartilage or tissue either instead of sutures or together with sutures.

The Bio-Gide® was un-covered in a class 100 laboratory and placed under aseptic conditions on the bottom of the wells in a NUNCLON™ Delta 6 well sterile disposable plate for cell research work (NUNC (InterMed) Roskilde, Denmark),—either with the porous surface of the bilayer membrane facing up or with the dense surface facing up. A number of approximately $10^6$ cells in 1 ml tissue culture medium containing serum was placed directly on top of the Bio-Gide®, dispersed either over the porous or the dense surface of the Bio-Gide®. The plate was then incubated in a $CO_2$ incubator at 37° C. for 60 minutes. An amount of 2 to 5 ml of tissue culture medium containing 5 to 7.5% serum was carefully added to the well containing the cells avoiding splashing the cells by holding the pipette tip tangential to the side of the well when expelling the medium.

On day 2 after the chondrocytes were placed in the well containing the Bio-Gide® the cells were examined in a Nikon Invert microscope. It was noticed that some chondrocytes had adhered to the edge of the Bio-Gide®. It was of course not possible to be able to look through the Bio-Gide® itself using this microscope.

The plate was incubated for 3 to 7 days with medium change at day 3. At the end of the incubation period the medium was decanted and cold refrigerated 2.5% glutaraldehyde containing 0.1M sodium salt of dimethylarsinic acid, also called sodium cacodylate, pH is adjusted with HCl to 7.4, was added as fixative for preparation of the cell and the Bio-Gide® supporter with the cells either cultured on the porous surface or the dense surface. The Bio-Gide® patches were then sent for electron microscopy at Department of Pathology, Herlev Hospital, Denmark.

The electron microscopy showed that the chondrocytes cultured on the dense surface of the Bio-Gide® did not grow into the collagen structure of the Bio-Gide®, whereas the cells cultured on the porous surface did indeed grow into the collagen structure and furthermore, showed presence of proteoglycans and no signs of fibroblast structures. This result showed us that when the collagen patch, as for instance a Bio-Gide® patch, is sewn as a patch covering a cartilage defect the porous surface of the collagen matrix should be facing down towards the defect in which the cultured chondrocytes are to be injected. They will then be able to penetrate the collagen and produce a smooth cartilage surface in line with the intact surface, and in this area a smooth layer of proteoglycans will be built up. Whereas, if the dense surface of the collagen patch is facing down into the defect the chondrocytes to be implanted will not integrate with the collagen, and the cells will not produce the same smooth surface as described above.

EXAMPLE 6

Chondrocytes were grown in minimal essential culture medium containing HAM F12 and 15 mM Hepes buffer and 5 to 7.5% autologous serum in a $CO_2$ incubator at 37° C. and handled in a Class 100 laboratory at Verigen Europe A/S, Symbion Science Park, Copenhagen, Denmark. The cells were trypsinized using trypsin EDTA for 5 to 10 minutes and counted using Trypan Blue viability staining in a Bürker-Türk chamber. The cell count was adjusted to $7.5 \times 10^5$ to $2 \times 10^6$ cells per ml. One NUNCLON plate was uncovered in the Class 100 laboratory.

The Bio-gide® used as a resorbable bilayer membrane may also be used together with an organic glue such as Tisseel® with additional, significantly higher content of Aprotinin than normally found in the Tisseel®, as described in the produc insert. By increasing the content of Aprotinin to about 25,000 KIU/ml, the resorption of the material will be delayed by weeks instead of the normal time span of days.

To test this feature in vitro, the Tisseel® is applied to the bottom of the well of the NUNCLON plate, and allowed to solidify incompletely. A collagen patch such as a Bio-Gide® is then applied over the Tisseel® and glued to the bottom of the well. This combination of Bio-Gide® and Tisseel® is designed to be a hemostatic barrier that will inhibit or prevent development or infiltration of blood vessels into the chondrocyte transplantation area. This hybrid collagen patch can now be used for both as a hemostatic barrier at the bottom of the lesion (most proximal to the surface to be reparied) but also as a support for cartilage formation because the distal surface can be the porous side of the collagen patch and thus encourage infiltration of chondrocytes and cartilage matrix. Thus this hybrid collagen patch can also be used to cover the top of the implant with the collagen porous surface directed towards the implanted chondrocytes and the barrier forming the top. The hybrid collagen patch, with elevated Aprotinin component may also be used without any organic glue such as Tisseel® and placed within the defect directly, adhering by natural forces. Thus the collagen patch can be used both as the hemostatic barrier, and the cell-free covering of the repair/transplant site, with the porous surfaces of the patches oriented towards the transplanted chondrocytes/cartilage. Another varient would use a collagen patch which consists of type II collagen (Geistlich Sohne AG, CH-6110 Wolhusen).

Thus the instant invention provides for a hybrid collagen patch where said patch is a collagen matrix with elevated levels of aprotinin component, preferably about 25,000 KIU/ml, in association with organic matix glue, where the collagen component is similar to the Bio-Gide® resorbable bilayer material or Type II collagen, and the organic glue is similar to the Tisseel® material. In another embodiment, the hybrid collagen patch does not use any organic glue to adhere to the site of repair.

EXAMPLE 7

A kit as envisioned, will allow for the convienent practice of the method of the instant invention. In a preferred embodiment, a kit of the invention will provide sterile components suitable for easy use in the surgical environment, and will provide a suitable hemostatic barrier, suitable covering patch, and if needed organic glue. A kit of the invention may also provide sterile, cell-free matrix material for supporting autologous chondrocytes that are to be implanted into an articular joint surface defect. In one embodiment, a kit of the invention contains a Surgicel® hemostatic barrier and a Bio-Gide® covering patch with suitable coating of Tissel® organic glue, where the Surgicel® and Bio-Gide® have been treated according to the teachings of the invention to increase the time till resorption. In instances where Tissel® is pre-coated, in one embodiment the Tissel® is supplemented with additional Aprotinin to increase time till resorption.

In another preferred embodiment, the hemostatic barrier and covering patch are both a semi-permeable collagen matrix which is treated to extend the time till resorption of the material. It is also possible to provide Tissel® glue in enhanced form as a separate component to be applied as needed because of the inherent variablility and unique circumstances every repair/transplantation procedure will encounter.

It will be appreciated by persons skilled in the art that numerous variations and/or modifications may be made to the invention shown in the specific embodiments without departing from the spirit or scope of the invention as broadly described. The present embodiements and examples are, therefore, to be considered in all respects as illustrative and not restrictive.

We claim:

1. A method for the effective treatment of articulating joint surface cartilage by the transplantation of chondrocytes in a suitable matrix, to a surface to be treated, the method comprising the steps:

(a) placing chondrocytes in a suitable matrix upon the surface to be treated; and (b) covering the surface to be treated with a covering-patch which is a semi-permeable collagen matrix with a porous surface.

2. The method according to claim 1, wherein the matrix is cell-free.

3. The method according to claim 2, wherein the porous surface of the covering-patch is directed toward the surface to be treated.

4. The method according to claim 1, wherein the covering-patch is substantially free of intact cells.

5. The method according to claim 1, wherein the covering-patch is resorbable.

6. The method according to claim 1, wherein the covering-patch is partially attached to the surface to be treated prior to placing of the chondrocytes in said suitable matrix on the surface to be treated in said step (b).

7. A kit for chondrocyte transplantation comprising a covering-patch which is a semi-permeable collagen matrix with a porous surface and an organic glue.

8. The kit according to claim 7 further comprising a matrix suitable for the placement of chondrocytes.

9. The kit according to claim 8 wherein the matrix is cell-free.

* * * * *